(12) United States Patent
Li et al.

(10) Patent No.: US 11,780,787 B2
(45) Date of Patent: Oct. 10, 2023

(54) METHOD FOR CONVERSION OF DIOLS TO OLEFIN PRODUCTS

(71) Applicants: UT-Battelle, LLC, Oak Ridge, TN (US); Triad National Security, LLC, Los Alamos, NM (US)

(72) Inventors: Zhenglong Li, Knoxville, TN (US); Andrew Sutton, Oak Ridge, TN (US); Cameron M. Moore, White Rock, NM (US); Michael Cordon, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 18/104,545

(22) Filed: Feb. 1, 2023

(65) Prior Publication Data

US 2023/0242464 A1 Aug. 3, 2023

Related U.S. Application Data

(60) Provisional application No. 63/305,817, filed on Feb. 2, 2022.

(51) Int. Cl.
*C07C 2/46* (2006.01)
*B01J 29/40* (2006.01)
*C07C 7/11* (2006.01)

(52) U.S. Cl.
CPC ............ *C07C 2/46* (2013.01); *B01J 29/40* (2013.01); *C07C 7/11* (2013.01)

(58) Field of Classification Search
CPC ............ C07C 2/46; C07C 7/11; B01J 29/40
See application file for complete search history.

(56) References Cited

U.S. PATENT DOCUMENTS 3,702,886 A   11/1972  Argauer et al.
3,725,438 A * 4/1973  Barone ............... C07D 317/12
                                                    549/430

(Continued)

*Primary Examiner* — Thuan D Dang
(74) *Attorney, Agent, or Firm* — Scully, Scott, Murphy & Presser, P.C.

(57) ABSTRACT

A method for converting a diol in solution to an olefin fraction, the method comprising: (i) reacting a diol of the formula HO—R—OH in solution with a carbonyl-containing molecule of the formula:

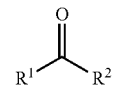

in the presence of an acid catalyst to result in a dioxolane molecule of the formula:

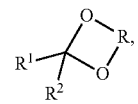

wherein R is a hydrocarbon linker containing 1-12 carbon atoms, and $R^1$ and $R^2$ are independently selected from hydrogen atom and hydrocarbon groups containing 1-12 carbon atoms, wherein $R^1$ and $R^2$ optionally interconnect; (ii) removing the dioxolane molecule from the solution by phase separation; and (iii) contacting the dioxolane molecule with a metal-loaded zeolite at a temperature of 100-500° C. to convert the dioxolane molecule to an olefin fraction.

27 Claims, 9 Drawing Sheets
(8 of 9 Drawing Sheet(s) Filed in Color)

(56) References Cited

U.S. PATENT DOCUMENTS

| | | | |
|---|---|---|---|
| 4,427,789 | A | 1/1984 | Miale et al. |
| 4,596,704 | A | 6/1986 | Miale et al. |
| 4,721,609 | A | 1/1988 | Baacke et al. |
| 5,314,665 | A | 5/1994 | Iwasa |
| 7,438,868 | B2 | 10/2008 | Kato |
| 7,442,425 | B2 | 10/2008 | Fu et al. |
| 7,459,413 | B2 | 12/2008 | Shen et al. |
| 9,181,493 | B2 | 11/2015 | Narula et al. |
| 10,300,474 | B2 | 5/2019 | Li |
| 11,053,181 | B2 | 7/2021 | Li |
| 2021/0107886 | A1 | 4/2021 | Sutton et al. |
| 2021/0122697 | A1* | 4/2021 | Frater .................. C07C 67/343 |

* cited by examiner

METHOD FOR CONVERSION OF DIOLS TO OLEFIN PRODUCTS

CROSS REFERENCE TO RELATED APPLICATION

The present application claims the benefit of U.S. Provisional Application No. 63/305,817, filed on Feb. 2, 2022, all of the contents of which are incorporated herein by reference.

GOVERNMENT SUPPORT

This invention was made with government support under Prime Contract No. DE-AC05-00OR22725 and DE-AC52-06NA25396 awarded by the U.S. Department of Energy. The government has certain rights in the invention.

FIELD OF THE INVENTION

The present invention generally relates to the catalytic conversion of butanediols to hydrocarbon fractions, particularly olefin products. The present invention more particularly relates to such catalytic conversion effected by zeolite-based catalysts.

BACKGROUND

Biomass fermentation to butanediols (particularly 2,3-butanediol, or BDO) is an important biological conversion pathway since butanediols are highly useful chemical building blocks for the production of a range of chemicals, including methyl ethyl ketone (MEK), 1,3-butadiene, and gamma-butyrolactone. Biomass fermentation to butanediols is generally accompanied by the co-production of acetoin and ethanol in water. Water content can be up to 90% in a typical butanediol fermentation mixture.

As fermentation occurs in aqueous solutions, the removal of BDO from water remains a primary challenge that limits the commercial viability of BDO upgrading, such as BDO conversion to hydrocarbons, including olefin products. One significant problem is the recovery of BDO or similar diol compounds from the dilute aqueous solutions in which they are produced. Typical water and alcohol separation strategies, such as distillation, are energy intensive and can easily inhibit large scale application of diols (especially BDO) for renewable fuels or chemical feedstock production. This is due to the high boiling point of BDO (~177° C.) which requires boiling of large quantities of water to use distillation as a BDO separation strategy. There would be a significant advantage in a diol-to-hydrocarbon conversion method that could bypass the need for energy intensive separation of diols, such as BDO, from an aqueous solution.

SUMMARY OF THE DISCLOSURE

The present disclosure is directed to a more straightforward and less energy intensive method for catalytically converting a diol, such as 2,3-butanediol (2,3-BDO), to an olefin fraction. The method advantageously circumvents the need to separate the diol from the native solution by the energy intensive and costly means used in the art prior to converting the diol to an olefin fraction. The method achieves this by first converting the diol while in solution to a dioxolane by reaction of the diol with an aldehyde or ketone. By virtue of the reduced solubility of the dioxolane in the solution, the dioxolane can be easily removed from the solution by simple phase separation. Once separated, the resulting dioxolane is catalytically converted to olefin product as further described below.

More specifically, the method involves the following steps: (i) reacting a diol of the formula HO—R—OH in solution with a carbonyl-containing molecule of the formula:

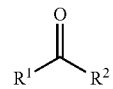

in the presence of an acid catalyst to result in a dioxolane molecule of the formula:

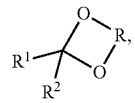

wherein R is a hydrocarbon linker containing 1-12 carbon atoms, and $R^1$ and $R^2$ are independently selected from hydrogen atom and hydrocarbon groups containing 1-12 carbon atoms, wherein $R^1$ and $R^2$ optionally interconnect; (ii) removing the dioxolane molecule from the solution by phase separation; and (iii) contacting the dioxolane molecule with a metal-loaded zeolite at a temperature of 100-500° C. to convert the dioxolane molecule to an olefin fraction.

In some embodiments, the solution is an aqueous solution, and the aqueous solution may contain water in an amount of at least 10, 20, 30, 40, or 50 wt %. In some embodiments, particularly in the event of the solution containing a lower amount of water (e.g., 10 wt % or less) or substantially no water, additional water may be added after dioxolane formation to facilitate the phase separation. The diol may be essentially any diol, such as 2,3-BDO, 1,4-BDO 2,5-pentanediol, ethylene glycol, or propylene glycol. In some embodiments, the diol is or includes 2,3-BDO in a fermentation mixture which typically also includes acetoin and/or ethanol, wherein the 2,3-BDO or other diol may be converted to a dioxolane directly in the fermentation mixture and separated from the fermentation mixture by simple phase separation. The carbonyl-containing molecule (e.g., aldehyde or ketone) may contain at least four carbon atoms (e.g., butyraldehyde, isobutyraldehyde, valeraldehyde, or benzaldehyde), in which case phase separation of the resulting dioxolane from an aqueous solution is typically spontaneous and does not require facilitation by addition of additional water. In other embodiments, the carbonyl-containing molecule may contain less than four carbon atoms, in which case phase separation of the resulting dioxolane may not be so spontaneous and may require facilitation, such as by adding water.

BRIEF DESCRIPTION OF THE DRAWINGS

The patent or application file contains at least three drawings executed in color. Copies of this patent or patent application publication with color drawing(s) will be provided by the Office upon request and payment of the necessary fee.

FIG. 1A is a generalized scheme for any diol and aldehyde/ketone combination. FIG. 1B is a specific scheme for 2,3-BDO and butyraldehyde conversion and their corresponding dioxolane intermediate.

DETAILED DESCRIPTION

Figure 1A:
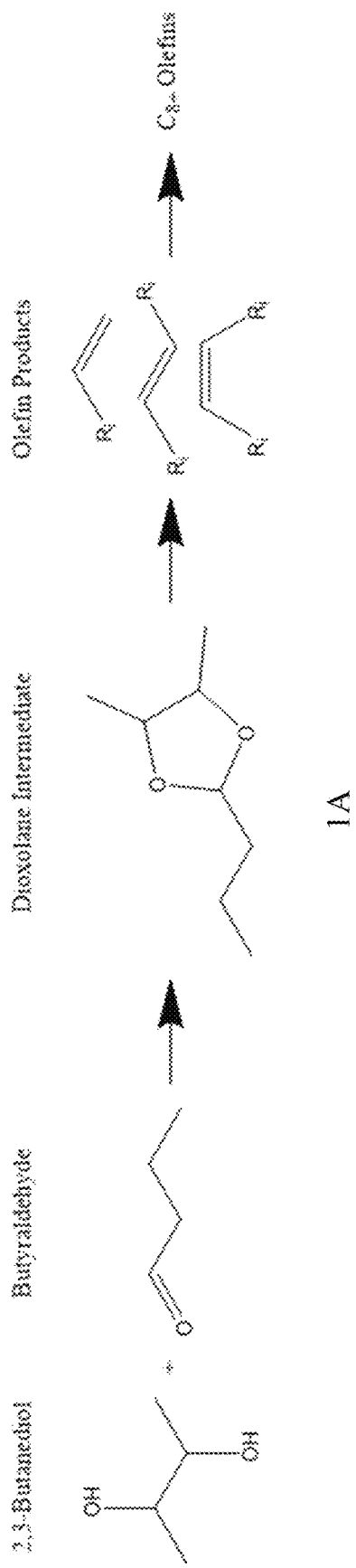
FIGS. 1A-1B. Schematics showing reaction pathways for the generation of long chain olefin products from diol and aldehyde/ketone reactants.

As used herein, the term "hydrocarbon group" is defined as a chemical group containing at least carbon and hydrogen atoms. The hydrocarbon group is typically composed solely of carbon and hydrogen, except that the hydrocarbon group may (i.e., optionally) be substituted with one or more fluorine atoms to result in partial or complete fluorination of the hydrocarbon group. In some embodiments, the hydrocarbon group may (or may not) contain an oxygen atom. An oxygen atom, if present, is typically an ether linkage or group. The hydrocarbon group (or linker) typically contains 1-12 carbon atoms. In different embodiments, one or more of the hydrocarbon groups in a molecule contain, for example, 1, 2, 3, 4, 5, 6, 7, 8, 9, 10, 11, or 12 carbon atoms, or a number of carbon atoms within a particular range bounded by any two of the foregoing carbon numbers (e.g., 1-12, 1-8, 1-6, 1-5, 1-4, 1-3, 2-12, 2-8, 2-6, 2-5, 2-4, or 2-3 carbon atoms). Hydrocarbon groups in different compounds described herein, or in different generic groups of a compound, may possess the same or different number (or preferred range thereof) of carbon atoms. For example, as further discussed below, any one of R$^1$ and R$^2$ in any of the generic formulas disclosed herein may independently contain a number of carbon atoms within any of the ranges provided above.

In a first set of embodiments, the hydrocarbon group is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, and n-dodecyl groups.

In a second set of embodiments, the hydrocarbon group is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl groups, isoheptyl, isooctyl, and the numerous other branched alkyl groups having up to 12 carbon atoms, wherein the "1-yl" suffix represents the point of attachment of the group.

In a third set of embodiments, the hydrocarbon group is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl (CH$_2$=CH—CH$_2$—CH$_2$—), 2-buten-1-yl (CH$_2$—CH=CH—CH$_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 12 carbon atoms.

In a fifth set of embodiments, the hydrocarbon group is unsaturated and branched, i.e., a branched olefinic or alkenyl group. Some examples of branched olefinic groups include propen-2-yl (CH$_2$=C·—CH$_3$), 1-buten-2-yl (CH$_2$=C·—CH$_2$—CH$_3$), 1-buten-3-yl (CH$_2$=CH—CH·—CH$_3$), 1-propen-2-methyl-3-yl (CH$_2$=C(CH$_3$)—CH$_2$—), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 12 carbon atoms, wherein the dot in any of the foregoing groups indicates a point of attachment.

In a sixth set of embodiments, the hydrocarbon group is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. All of the foregoing cyclic groups are carbocyclic groups.

As used herein, the term "hydrocarbon linker" is a linking group containing 1-12 carbon atoms and which can be derived from any of the hydrocarbon groups described above by removing a hydrogen atom from the hydrocarbon group. For example, a hydrogen atom may be removed from an ethyl group (—CH$_2$CH$_3$) to result in an ethylene (—CH$_2$CH$_2$—) linker. Hydrocarbon linkers disclosed in this application may independently have any of the carbon numbers provided above and may be derived from any of the linear or branched alkyl, alkenyl, or alkynyl groups described above or saturated or unsaturated cyclic groups described above, and may or may not contain one or more fluorine atoms and/or an oxygen atom.

The term "diol", as used herein, includes molecules containing two hydroxy (OH) groups bound to a hydrocarbon linking portion (R) containing 1-12 carbon atoms. As discussed above, R is typically composed solely of carbon and hydrogen atoms except that R may be substituted with one or more fluorine atoms and/or contain an oxygen atom. The diol can be conveniently represented by the following formula:

HO—R—OH  (1)

In Formula (1) above, R can be any of the hydrocarbon linkers described above containing 1-12 carbon atoms or any sub-range therein, as provided above. Typically, R is a linear or branched alkylene linker containing 1-12 carbon atoms or any sub-range therein, as provided above. The linker R may more particularly be represented by the formula —$(CH_2)_n$—, wherein n is 1-12 and one or more hydrogen atoms in the formula may be substituted with a methyl or ethyl group to result in a branched alkylene linker. The hydrocarbon linker (R), whether linear or branched, typically contains no more than 12 carbon atoms. Some particular examples of linear alkylene linkers include methylene (—$CH_2$—), 1,2-ethylene (—$CH_2CH_2$—), 1,3-n-propylene (—$CH_2CH_2CH_2$—), 1,4-n-butylene, 1,5-n-pentylene, 1,6-n-hexylene, 1,7-n-heptylene, 1,8-n-octylene, 1,9-nonylene, 1,10-decylene, 1,11-undecylene, and 1,12-dodecylene. Some particular examples of branched alkylene linkers include 1,2-propylene (—$CH(CH_3)CH_2$—), 1,2-butylene (—$CH(CH_2CH_3)CH_2$—), 1,3-butylene (—$CH(CH_3)CH_2CH_2$—), and 2,3-butylene (—$CH(CH_3)CH(CH_3)$—). Notably, when R is 2,3-butylene, the resulting diol is 2,3-BDO. In some embodiments, R excludes aromatic rings (e.g., phenyl) or R excludes unsaturated linkers altogether. In some embodiments, the diol is selected from one or more of 2,3-BDO, 1,4-BDO, 2,5-pentanediol, ethylene glycol, and propylene glycol.

The carbonyl-containing compound can be conveniently represented by the following formula:

(2)

In Formula (2) above, $R^1$ and $R^2$ are independently selected from hydrogen atoms and any of the hydrocarbon groups described above containing 1-12 carbon atoms or any sub-range therein, as provided above. In some embodiments, $R^1$ and $R^2$ are both hydrogen atoms, in which case the carbonyl-containing molecule is formaldehyde. In other embodiments, one of $R^1$ and $R^2$ is a hydrogen atom and the other one of $R^1$ and $R^2$ is a hydrocarbon group, in which case the carbonyl-containing molecule is an aldehyde. In other embodiments, both $R^1$ and $R^2$ are independently selected from hydrocarbon groups, in which case the carbonyl-containing molecule is a ketone. In some embodiments, one or both of $R^1$ and $R^2$ are linear or branched alkyl groups containing 1-12 carbon atoms or any sub-range therein, as provided above. $R^1$ and/or $R^2$ may more particularly be represented by the formula —$(CH_2)_nCH_3$, wherein n is 1-11 and one or more hydrogen atoms in the formula may be substituted with a methyl or ethyl group to result in a branched alkyl group. $R^1$ and $R^2$, whether linear or branched, typically contain no more than 12 carbon atoms. Some particular examples of linear alkyl groups for $R^1$ and/or $R^2$ include methyl, ethyl, n-propyl, n-butyl, n-pentyl, n-hexyl, n-heptyl, n-octyl, n-nonyl, n-decyl, n-undecyl, and n-dodecyl groups. Some particular examples of branched alkyl groups for $R^1$ and/or $R^2$ include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl groups, isoheptyl, isooctyl, and the numerous other branched alkyl groups having up to 12 carbon atoms, wherein the "1-yl" suffix represents the point of attachment of the group.

Some particular examples of aldehydes within the scope of Formula (2) include formaldehyde, acetaldehyde, propionaldehyde, butyraldehyde, isobutyraldehyde, valeraldehyde, isovaleraldehyde, hexanaldehyde, heptanaldehyde, octanaldehyde, nonanaldehyde, decanaldehyde (decanal), undecanaldehyde (undecanal), dodecanaldehyde (dodecanal), 2-methylhexanaldehyde, 2-ethylhexanaldehyde, furfural, benzaldehyde, methylbenzaldehydes, cinnamaldehyde, naphthyl aldehydes, and retinaldehyde. Some particular examples of ketones within the scope of Formula (2) include acetone (dimethyl ketone), methyl ethyl ketone, diethyl ketone, methyl propyl ketone, methyl butyl ketone, methyl pentyl ketone, methyl hexyl ketone, methyl heptyl ketone, methyl octyl ketone, di(n-propyl)ketone, di(n-butyl) ketone, di-(n-pentyl)ketone, di(n-hexyl)ketone, ethyl propyl ketone, ethyl butyl ketone, ethyl pentyl ketone, ethyl hexyl ketone, ethyl heptyl ketone, ethyl octyl ketone, propyl butyl ketone, propyl isobutyl ketone, methyl phenyl ketone (acetophenone), and diphenyl ketone. Some examples of cyclic ketones resulting from interconnection of $R^1$ and $R^2$ in Formula (2) include cyclopentanone, cyclohexanone, and 2-furanone. In some embodiments, $R^1$ and $R^2$ in Formula (2) are not permitted to interconnect.

Any of the diols described earlier above may be reacted with any of the above carbonyl-containing molecules to produce a dioxolane molecule. In particular embodiments, the dioxolane molecule is a 1,3-dioxolane (1,3-dioxacyclopentane), or more specifically, a 4-methyl-1,3-dioxolane or 4,5-dimethyl-1,3-dioxolane, any of which may be substituted with one or two hydrocarbon groups at the 2-position of the 1,3-dioxolane ring depending on the structure of the carbonyl-containing molecule used in making the dioxolane. Some examples of dioxolane molecules include 4,5-dimethyl-1,3-dioxolane, 2,4,5-trimethyl-1,3-dioxolane, 4,5-dimethyl-2-ethyl-1,3-dioxolane, 4,5-dimethyl-2-propyl-1,3-dioxolane, 4,5-dimethyl-2-(propan-3-yl)-1,3-dioxolane, 4,5-dimethyl-2-pentyl-1,3-dioxolane, 4,5-dimethyl-2-(pentan-3-yl)-1,3-dioxolane, 4,5-dimethyl-2-heptyl-1,3-dioxolane, 2-(heptan-3-yl)-4,5-dimethyl-1,3-dioxolane, 2-furanyl-4,5-dimethyl-1,3-dioxolane, 2-cyclohexyl-4,5-dimethyl-1,3-dioxolane, 2-phenyl-4,5-dimethyl-1,3-dioxolane, 2-ethyl-2,4,5-trimethyl-1,3-dioxolane, 2-hexyl-2,4,5-trimethyl-1,3-dioxolane, and 2,2,4,5-tetramethyl-1,3-dioxolane. Although the term "dioxolane" may, in some embodiments, refer to molecules of Formula (2) containing a 1,3-dioxacyclopentane ring, the term "dioxolane", as used herein, is meant to more broadly encompass any 1,3-dioxa hydrocarbon (typically, saturated) ring, such as a 1,3-dioxacyclohexane (1,3-dioxane) ring or 1,3-dioxacycloheptane ring. A 1,3-dioxacyclohexane (1,3-dioxane) ring may result from the reaction of, for example, 1,3-propanediol, 1,3-butanediol, 1,3-pentanediol, or 1,3-hexanediol with an aldehyde or ketone. Similarly, a 1,3-dioxacycloheptane ring may result from the reaction of, for example, 1,4-butanediol, 1,4-pentanediol, or 1,4-hexanediol with an aldehyde or ketone.

In a first step of the method, the diol, as described above, is reacted with a carbonyl-containing compound, as described above, in the presence of an acid catalyst to form a dioxolane compound. Typically, the diol and carbonyl-containing compound are mixed, either in solution or in neat form, and placed in contact with an acid catalyst at room temperature (typically about 20 or 25° C.) or at an elevated temperature. When performed in solution, the solvent may be, for example, water or an ether solvent. In some embodiments, the solution is an aqueous solution, and the aqueous solution may contain water in an amount of at least 10, 20, 30, 40, or 50 wt %. Depending on the starting materials and nature of the solvent (if any), the elevated temperature may be, for example, at least 30, 35, 40, 45, 50, 60, 70, 80, 90, or 100° C., or a temperature within a range bound by any two of the foregoing temperatures. The acid catalyst may be any of the acid catalysts known in the art, including solid and liquid acid catalysts. Some examples of solid acid catalysts include Nafion, Amberlyst, zeolite catalysts (e.g., such as MCM-22 or large pore zeolite, e.g., H-beta), sulfated zirconia (VI), montmorillonite K10, amorphous silico-aluminate catalysts, heteropolyoxometallates, sulfonated polystyrene, solid phosphoric acid, and niobic acid, all of which are well known in the art. Some examples of liquid acid catalysts include sulfuric acid, sulfonic acids, hydrochloric acid, and nitric acid.

In the reaction for producing the dioxolane, the diol and carbonyl-containing compound can be included in any suitable ratio, except that the carbonyl-containing compound is typically included in a higher amount compared to the diol. The ratio of carbonyl-containing compound to diol may be in a range of, for example, 10:1 to 1:1, or more particularly, 10:1 to 2:1, or 8:1 to 1:1, or 8:1 to 2:1, or 5:1 to 1:1, or 5:1 to 2:1 or 5:1 to 3:1, wherein the term "ratio" may be weight ratio or molar ratio.

In some embodiments, the diol is or includes 2,3-BDO in a fermentation mixture that also includes acetoin and/or ethanol. The 2,3-BDO or other diol may be converted to a dioxolane directly in the fermentation mixture and separated from the fermentation mixture by simple phase separation, as further discussed below.

In a next step of the method, the dioxolane molecule is removed from the solution by phase separation. By virtue of the greater hydrophobicity of the dioxolane molecule compared to the diol or aldehyde/ketone, the dioxolane molecule can spontaneously separate from the solution or neat form. In some embodiments, particularly in the event of the solution containing a lower amount of water (e.g., 10 wt % or less) or substantially no water, additional water may be added after dioxolane formation to facilitate the phase separation. The carbonyl-containing molecule (e.g., aldehyde or ketone) may contain at least four carbon atoms (e.g., butyraldehyde, isobutyraldehyde, valeraldehyde, benzaldehyde, other described earlier above), in which case phase separation of the resulting dioxolane from an aqueous solution is typically spontaneous and does not require facilitation by addition of additional water. In other embodiments, the carbonyl-containing molecule may contain less than four carbon atoms, in which case phase separation of the resulting dioxolane may not be so spontaneous and may require facilitation, such as by adding water.

In some embodiments, after step (ii) but before step (iii), the dioxolane molecule is washed with water or an aqueous solution in which the dioxolane molecule is substantially or completely insoluble. In some embodiments, the dioxolane molecule is washed with a bicarbonate solution, which may be a saturated bicarbonate solution. In other embodiments, the dioxolane molecule is washed with a solution (which may be a saturated solution) of an alkali or alkaline earth salt, e.g., sodium chloride, sodium bromide, sodium sulfate, sodium nitrate, potassium chloride, potassium bromide, potassium sulfate, magnesium chloride, magnesium bromide, or magnesium sulfate. In some embodiments, after step (ii) but before step (iii), the dioxolane molecule is substantially removed of water. The dioxolane molecule can be removed of water by any of the means well known in the art, such as by contacting the dioxolane with anhydrous sodium sulfate, magnesium sulfate, or calcium chloride.

In a subsequent step, the dioxolane molecule is contacted with a metal-loaded zeolite at an elevated temperature to convert the dioxolane molecule to an olefin fraction. In the process, a suitable reaction temperature is employed during contact of the dioxolane with the zeolite catalyst. Generally, the reaction temperature is at least 100° C. and up to 500° C. In different embodiments, the reaction temperature is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., or 500° C., or a temperature within a range bounded by any two of the foregoing exemplary temperatures, e.g., 100° C.-500° C., 200° C.-500° C., 300° C.-500° C., 350° C.-500° C., 400° C.-500° C., 100° C.-400° C., 200° C.-400° C., 300° C.-400° C., 100° C.-300° C., 200° C.-300° C., 250° C.-300° C., 100° C.-250° C., 150° C.-250° C., 175° C.-250° C., or 100° C.-200° C.). Generally, ambient (i.e., normal atmospheric) pressure of about 1 atm is used in the method described herein. However, in some embodiments, an elevated pressure or reduced pressure may be used. For example, in some embodiments, the pressure may be elevated to, for example, 1.5, 2, 3, 4, or 5 atm, or reduced to, for example, 0.5, 0.2, or 0.1 atm.

The metal-loaded zeolite includes a zeolite portion (i.e., zeolite phase) and a metal loaded into the zeolite. Any of the zeolites known in the art for BDO upgrading should work for dioxolane conversion to olefin. The catalyst is composed of a zeolite loaded with at least one metal catalytically active for converting the dioxolane molecule to an olefin fraction. The at least one catalytically active metal may be selected from, for example, copper, silver, gold, nickel, palladium, platinum, rhodium, iridium, and ruthenium, or a mixture or alloy of any two or three thereof (e.g., a CuAg alloy). In some embodiments, any one or more of the foregoing metals may be excluded. Other metals, such as iron (Fe), cobalt (Co), scandium (Sc), vanadium (V), or lanthanum (La), may be included or excluded. The catalytically active metal may be present in an amount of 1-30 wt % by weight of the zeolite. The total amount of any one or more of the foregoing active metals that are present in the catalyst may be, for example, 1, 2, 5, 10, 15, 20, 25, or 30 wt %, or in an amount within a range bounded by any two of the foregoing amounts.

The zeolite can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. The zeolite may be a medium-pore or large-pore zeolite. In particular embodiments, the zeolite is stable from at least 100° C. and up to 700° C. Typically, the zeolite is ordered by having a crystalline or partly crystalline structure. The zeolite can be generally described as a three-dimensional framework containing silicate ($SiO_2$ or $SiO_4$) and aluminate ($Al_2O_3$ or $AlO_4$) units that are interconnected (i.e., crosslinked) by the sharing of oxygen atoms. The zeolite can be microporous (i.e., pore size of less than 2 μm), mesoporous (i.e., pore size within 2-50 μm, or sub-range therein), or a combination thereof. Although the term "zeolite" technically refers to aluminosilicates, the term "zeolite," as used herein, may refer to solid compositions having a zeolite type of structure but which is not technically a zeolite, such as alumina or silica or mixture thereof.

The zeolite can be microporous (i.e., pore size of less than 2 μm), mesoporous (i.e., pore size within 2-50 μm, or sub-range therein), or a combination thereof. In some embodiments, the zeolite phase is completely or substantially microporous. By being completely or substantially microporous, the pore volume due to micropores can be, for example, 100%, or at least 95%, 96%, 97%, 98%, 99%, or 99.5%, with the remaining pore volume being due to mesopores, or in some embodiments, macropores (pore size greater than 50 μm). In other embodiments, the zeolite phase is completely or substantially mesoporous. By being completely or substantially mesoporous, the pore volume due to mesopores can be, for example, 100%, or at least 95%, 96%, 97%, 98%, 99%, or 99.5%, with the remaining pore volume being due to micropores, or in some embodiments, macropores. In yet other embodiments, the zeolite phase contains an abundance of both micropores and mesopores. By containing an abundance of both micropores and mesopores, the pore volume due to mesopores can be, for example, up to, at least, or precisely 50%, 60%, 70%, 80%, or 90%, with the pore volume balance being due to micropores, or vice-versa.

The zeolite can have any suitable silica-to-alumina (i.e., $SiO_2/Al_2O_3$ or "Si/Al") ratio. In some embodiments, the zeolite composition is partially dealuminated and has a silicon to aluminum ratio of at least or above 10, or the dealuminated zeolite composition does not contain aluminum (i.e., is completely dealuminated and composed of only silicon oxide, and optionally, one or more other elements in a trace amount). In various embodiments, the zeolite can have a Si/Al ratio of precisely, at least, more than, less than, or up to 10, 11, 12, 13, 14, 15, 20, 25, 30, 35, 40, 45, 50, 55, 60, 65, 70, 75, 80, 85, 90, 95, 100, 120, 150, 200, 300, 400, 500, 600, 700, 800, 900, 1000, 1100, 1200, 1300, 1400, or 1500, or a Si/Al ratio within a range bounded by any two of the foregoing values. As aluminum is present in any of the foregoing zeolite compositions having any of the recited Si/Al ratios, any such zeolite is herein considered to be partially dealuminated. The zeolite may also be completely dealuminated, in which case the zeolite does not contain aluminum, and thus, cannot have a Si/Al ratio. In some embodiments, the zeolite is at least partially dealuminated and has a Si/Al ratio of at least or above 10, 15, 20, 25, or 30, including any of the Si/Al ratios over 30 provided above.

In various embodiments, the zeolite (whether aluminated, partially dealuminated, or completely dealuminated) is a MFI-type zeolite, MWW-type zeolite, MEL-type zeolite, MTW-type zeolite, MCM-type zeolite, BEA-type (beta) zeolite, kaolin, or a faujasite-type of zeolite. Some particular examples of zeolites include the pentasil zeolites, and more particularly, the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta, and the MCM class of zeolites (e.g., MCM-22, MCM-41, and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety. In particular embodiments, the zeolite is ZSM-5. ZSM-5 belongs to the pentasil-containing class of zeolites, all of which are also considered herein. In particular embodiments, the ZSM-5 zeolite is represented by the formula $Na_nAl_nSi_{96-n}O_{192} \cdot 16H_2O$, wherein $0<n<27$. In some embodiments, the zeolite is a 2D pillared zeolite, as well known in the art. The 2D pillared zeolite can be a 2D pillared version of any of the zeolites described above, such as a pillared MFI or MWW zeolite.

Typically, the zeolite contains an amount of cationic species, aside from active metal species. As is well known in the art, the amount of cationic species is generally proportional to the amount of aluminum in the zeolite. This is because the replacement of silicon atoms with lower valent aluminum atoms necessitates the presence of counter-cations to establish a charge balance. Some examples of cationic species include hydrogen ions ($H^+$), alkali metal ions, alkaline earth metal ions, and main group metal ions. Some examples of alkali metal ions that may be included in the zeolite include lithium ($Li^+$), sodium ($Na^+$), potassium ($K^+$), rubidium ($Rb^+$), and cesium ($Cs^+$). Some examples of alkaline earth metal ions that may be included in the zeolite include ($Be^{2+}$), magnesium ($Mg^{2+}$), calcium ($Ca^{2+}$), strontium ($Sr^{2+}$), and barium ($Ba^{2+}$). Some examples of main group metal ions that may be included in the zeolite include boron ($B^{3+}$), gallium ($Ga^{3+}$), indium ($In^{3+}$), and arsenic ($As^{3+}$). In some embodiments, a combination of cationic species is included. The cationic species can be in a trace amount (e.g., no more than 0.01 or 0.001%), or alternatively, in a significant amount (e.g., above 0.01%, and up to, for example, 0.1, 0.5, 1, 2, 3, 4, or 5% by weight of the zeolite). In some embodiments, any one or more of the above classes or specific examples of cationic species are excluded from the zeolite.

Generally, the zeolite described herein is in the form of a powder. In a first set of embodiments, at least a portion, or all, of the particles of the powder have a size less than a micron (i.e., nanosized particles). The nanosized particles can have a particle size of precisely, at least, up to, or less than, for example, 1, 2, 5, 10, 20, 30, 40, 50, 60, 70, 80, 90, 100, 150, 200, 250, 300, 350, 400, 450, 500, 550, 600, 650, 700, 750, 800, 850, 900, or 950 nanometers (nm), or a particle size within a range bounded by any two of the foregoing values. In a second set of embodiments, at least a portion, or all, of the particles of the zeolite powder have a size at or above 1 micron in size. The micron-sized particles can have a particle size of precisely, at least, up to, or less than, for example, 0.25, 0.5, 1, 2, 5, 10, 20, 30, 40, 50, 60, 70, 80, 90, or 100 microns (μm), or a particle size within a range bounded by any two of the foregoing values. In some embodiments, single crystals or grains of the zeolite correspond to any of the sizes provided above, while in other embodiments, crystals or grains of the zeolite are agglomerated to provide agglomerated crystallites or grains having any of the above exemplary dimensions.

In other embodiments, the zeolite can be in the form of a film, a coating, or a multiplicity of films or coatings. The thickness of the coatings or multiplicity of coatings can be, for example, 1, 2, 5, 10, 50, or 100 microns, or a range therein, or up to 100 micron thickness. In yet other embodiments, the zeolite is in the form of a non-particulate (i.e., continuous) bulk solid. In still other embodiments, the zeolite can be fibrous or in the form of a mesh.

The zeolite (with metal incorporated therein) can also be mixed with or affixed onto a support material, such as one suitable for operation in a catalytic converter. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), zirconia, or a carbide (e.g., silicon carbide), or a combination thereof. Honeycomb structures, in particular, are described in detail in, for example, U.S. Pat. Nos. 5,314,665, 7,442,425, and 7,438,868, the contents of which are incorporated herein by reference in their entirety. When corrugated or other types of metal sheets are used, these can be layered on top of each other with catalyst material supported on the sheets such that passages remain that allow the flow of alcohol-containing fluid. The layered sheets can also be formed into a structure, such as a cylinder, by winding the sheets.

The catalyst and reactor can have any of the designs known in the art for catalytically treating a fluid or gas at elevated temperatures, such as a fluidized bed reactor. The process may be in a continuous or batch mode. In particular embodiments, the one or more organic species are injected into a heated reactor such that the one or more organic species are quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate one or more organic species because the distillation process removes the dissolved solids in the fermentation streams. The boiler unit volatilizes liquid feedstock into gases prior to entry into the reactor unit and withholds dissolved solids.

In particular embodiments, the zeolite is or includes a pentasil-type composition loaded with any of the suitable metals described above. In more specific embodiments, the zeolite is, or includes, for example, copper-loaded ZSM5 (i.e., Cu-ZSM5), copper-loaded BEA, copper-loaded MFI, Fe-ZSM5, Cu,Fe-ZSM5, or a mixture of Cu-ZSM5 and Fe-ZSM5. In other embodiments, the zeolite is, or includes, for example, Cu—La—ZSM5, Fe—La—ZSM5, Fe—Cu—La—ZSM5, Cu—Sc—ZSM5, or Cu—In-ZSM5.

In some embodiments, the dioxolane-to-olefin conversion step is performed in the presence of a carrier gas. In some embodiments, the carrier gas is an inert gas, such as nitrogen or argon, or a mixture thereof. In other embodiments, the carrier gas is a reducing gas, such as hydrogen gas. Hydrogen partial pressures can range from 0-100% $H_2$ carrier gas.

As indicated above, the method produces an olefin (alkene) fraction. The olefin fraction typically contains a range of different olefin molecules. However, the method may, under some conditions, produce a more limited number of olefins, such as strictly one, two, or three types of olefin molecules. The olefin fraction is typically composed of $C_2$-$C_{10}$, $C_2$-$C_9$, or $C_2$-$C_8$ mixed olefins, i.e., alkenes containing 2-10, 2-9, or 2-8 carbon atoms, respectively (particularly $C_4$ unsaturated compounds, and more particularly, the butenes). In some embodiments, the olefin fraction contains $C_3$-$C_{10}$, $C_3$-$C_9$, or $C_3$-$C_8$ mixed olefins (i.e., with $C_2$ olefin substantially or completely absent). The present method is particularly capable of producing $C_4^+$ alkenes (e.g., butenes, pentenes, hexenes, heptenes, octenes, nonenes, and decenes). Some examples of $C_4^+$ alkenes include 1-butene, 2-butene, 1,3-butadiene, 1-pentene, cis-2-pentene, trans-2-pentene, isopentene (3-methyl-1-butene), 1-hexene, cis-2-hexene, trans-2-hexene, cis-3-hexene, trans-3-hexene, isohexene (4-methyl-1-pentene), 3-methyl-1-pentene, 3,4-dimethyl-1-pentene, 1-heptene, isoheptene (5-methyl-1-hexene), 4-methyl-1-hexene, 1-octene, 2,4,4-trimethyl-1-pentene. The methods described herein may produce one or more of any of the foregoing compounds. In some embodiments, by appropriate choice of the catalyst and process conditions (e.g., temperature), the method produces predominantly one type of product, wherein the term "predominantly" generally corresponds to a yield of greater than 50%, although, in some cases, a yield of at least 40%, 45%, or 50% may correspond to a predominant amount. In some embodiments, the yield for any one or more of the foregoing compounds may be at least or greater than, for example, 20%, 25%, 30%, 35%, 40%, 45%, 50%, 55%, 60%, 65%, 70%, 75%, 80%, 85%, or 90%.

In some embodiments, $C_2$-$C_{10}$, $C_2$-$C_9$, or $C_2$-$C_8$ mixed olefins are produced in at least or greater than 30%, 35%, 40%, 45%, 50%, 55%, 60%, 65%, 70%, 75%, 80%, 85%, or 90% yield. In some embodiments, the process produces $C_4$ unsaturated compounds (e.g., butenes) in at least or greater than 30%, 35%, 40%, 45%, 50%, 55%, 60%, 65%, or 70% yield; or the process achieves a selectivity in butenes of at least or greater than 30%, 35%, 40%, 45%, 50%, 55%, 60%, 65%, or 70%. In some embodiments, the process achieves less than 20% ethylene yield in the olefin fraction, or the process may achieve less than 15%, 10%, 5%, 4%, 3%, 2%, or 1% ethylene yield in the olefin fraction. In some embodiments, the process achieves no more than or less than 30%, 25%, 20%, 15%, 10%, 5%, 4%, 3%, 2%, or 1% of $C_2$-$C_3$ olefins. In some embodiments, the process produces $C_5^+$ olefins in at least or greater than 20%, 25%, 30%, 35%, 40%, 45%, 50%, 55%, 60%, 65%, 70%, or 75% yield; or the process achieves a selectivity in $C_5^+$ olefins of at least or greater than 20%, 25%, 30%, 35%, 40%, 45%, 50%, 55%, 60%, 65%, 70%, or 75%. In some embodiments, the process produces $C_6^+$ olefins in at least or greater than 10%, 15%, 20%, 25%, 30%, 35%, 40%, 45%, or 50% yield; or the process achieves a selectivity in $C_5^+$ olefins of at least or greater than 10%, 15%, 20%, 25%, 30%, 35%, 40%, 45%, or 50%. In some embodiments, the process produces $C_7^+$, $C_8^+$, or $C_9^+$ olefins in at least or greater than 5%, 10%, 15%, 20%, 25%, 30%, 35%, 40%, 45%, or 50% yield; or the process achieves a selectivity in $C_7^+$, $C_8^+$, or $C_9^+$ olefins of at least or greater than 5%, 10%, 15%, 20%, 25%, 30%, 35%, or 40%. In further or separate embodiments, the process achieves no more than or less than 30%, 25%, 20%, 15%, 10%, 5%, 4%, 3%, 2%, or 1% of $C_1$-$C_3$ paraffins.

In some embodiments, the conversion method described above is integrated with a biomass-to-butanediol fermentation process, wherein the fermentation process produces 2,3-BDO (and optionally, one or more other diols) typically along with one or more organic species. By being "integrated" is meant that the fermentation solution or one or more diols obtained from the fermentation solution, as produced in a fermentation facility or zone, is sent to and processed at a conversion facility or zone that performs the conversion process described above. Preferably, in order to minimize production costs, the fermentation process is in close enough proximity to the conversion facility or zone, or includes appropriate conduits for transferring produced organic compounds to the conversion facility or zone, thereby not requiring the organic compounds to be shipped. In particular embodiments, the fermentation stream produced in the fermentation facility is directly transferred to the conversion facility, generally with removal of solids from the raw stream (generally by filtration or settling) before contact of the stream with the zeolite catalyst.

In some embodiments, the fermentation process is performed in an autonomous fermentation facility, i.e., where saccharides, produced elsewhere, are loaded into the fermentation facility to produce the one or more organic species. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass generally refers to lignocellulosic matter (i.e., plant material), such as wood, grass, leaves, paper, corn husks, sugar cane, bagasse, and nut hulls. Generally, biomass-to-butanediol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, by the action of an organism capable of fermenting saccharide to 2,3-butanediol. In other embodiments, the one or more organic species are produced from a more direct sugar source, such as a plant-based source of sugars, such as sugar cane or a grain starch (such as corn starch).

The present disclosure is also directed to methods for further converting the olefins, as produced by the conversion process, to a synthetic fossil fuel (e.g., jet fuel), fuel additive, or commodity chemical. To effect the further conversion, the olefins are reacted with one or more additional catalysts known in the art capable of such transformation. The additional catalyst may be, for example, a zeolite (e.g., H-BEA, H-ZSM-5, MCM, H-ZSM-22, or H-ZSM-57), amorphous aluminosilicate, sulfonic acid ion-exchange resin (e.g., Amberlyst® 15, Amberlyst® 35, Amberlyst® 36, Purolite®, Dowex®, Lewatit®), or solid phosphoric acid. The conditions of the reaction may be, for example, 100-500° C. (or more particularly, 70-350° C.), 1-60 atm, a weight hourly space velocity (WHSV) of 0.1 $h^{-1}$ to 20 $h^{-1}$, and an inert or hydrogen carrier gas. The foregoing catalysts and conditions are generally suited for a dimerization, oligomerization, or dehydrocyclization process. However, the process may also include a hydrogenation process, which may employ an oxide catalyst (e.g., $Al_2O_3$, $TiO_2$, $CeO_2$, or $ZrO_2$) coated or impregnated with platinum (Pt), nickel (Ni), rhodium (Rh), ruthenium (Ru) or other noble metal or precious metal. In some embodiments, zinc (Zn) or phosphorus (P) is included in the zeolite (e.g., ZSM-5) to make the catalyst more selective for converting olefins (or specifically, butenes) to one or more of benzene, toluene, and xylenes (particularly p-xylene). In some embodiments, the oligomerization and hydrogenation occur simultaneously, while in other embodiments, the oligomerization and hydrogenation occur in separate steps.

The term "synthetic fossil fuel" refers to a mixture of hydrocarbon compounds useful as a fuel or as a blendstock in a fuel. The mixture of hydrocarbon compounds produced herein substantially corresponds (e.g., in composition and/or properties) to a known petrochemical fuel, such as petroleum, or a fractional distillate of petroleum. Some examples of petrochemical fuels include jet fuel (i.e., jet propellant, such as JP-8), gasoline, kerosene, and diesel. Like hydrocarbon fuel grades in current use, the mixture of hydrocarbon compounds produced herein can, in some embodiments, be predominantly or exclusively composed of alkenes, with minor amounts of aromatics or paraffins possible. In some embodiments, aromatics (e.g., benzene, toluene, and/or xylenes) are substantially or completely absent in the olefin fraction as produced upon conversion. Although aromatics (particularly benzene) may be present in the hydrocarbon mixture, their presence may be minimized to adhere to current fuel standards. Aromatics may be present in an amount of no more than 1%, 0.5%, 0.2%, or 0.1%. The raw hydrocarbon product may also be fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the dioxolane, composition of the catalyst (e.g., catalytic metal), amount of catalyst (e.g., ratio of catalyst to alcohol precursor), processing temperature, and flow rate (e.g., LHSV).

Examples have been set forth below for the purpose of illustration and to describe certain specific embodiments of the invention. However, the scope of this invention is not to be in any way limited by the examples set forth herein.

Examples

Overview

Figure 1B:
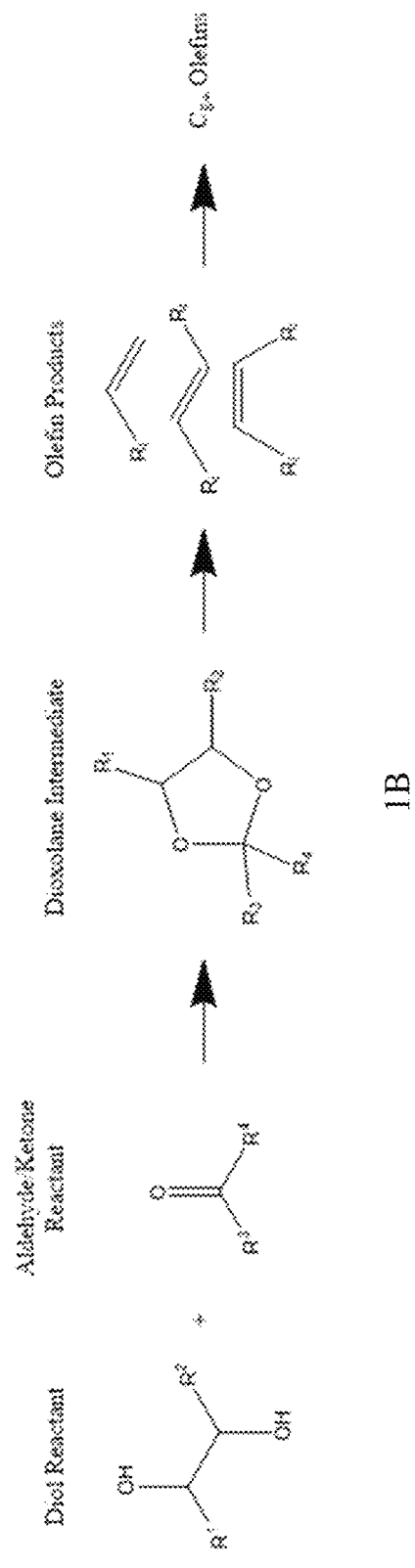

BDO can be converted into dioxolane compounds in aqueous solutions using aldehyde or other carbonyl-containing molecules. These dioxolanes naturally phase separate from the aqueous solution which allows for their separation from water. FIGS. 1A and 1B schematically show possible reaction pathways for the generation of long-chain olefin products from diol and aldehyde/ketone reactants. FIG. 1A provides a generalized scheme for any diol and aldehyde/ketone combination. FIG. 1B provides a specific scheme for 2,3-BDO and butyraldehyde conversion and the corresponding dioxolane intermediate.

The technology described herein provides a process for converting dioxolane compounds into olefins. Dioxolane generation from diols can be performed by any suitable method, such as the process described below.

Generally, a diol, such as BDO, is reacted with an aldehyde, ketone, or other carbonyl-containing molecule to form a dioxolane. The dioxolane can be removed from the aqueous feed as necessary. The dioxolane is then converted into olefins (such as, for example, two molar equivalents of olefins) using the process described herein for converting dioxolanes into olefins. The process can further include downstream upgrading strategies, such as oligomerization, to generate fuel-range hydrocarbons or other higher value chemical products.

After forming the dioxolane, the separation and/or purification of the dioxolane is highly favorable (e.g., by decanting) and, when the dioxolane is formed directly in an aqueous feed and/or the fermentation broth, this step removes the need for expensive water extraction methods, such as distillation to isolate BDO and water, wherein BDO has a high boiling point relative to water. This separation process instead leverages the natural phase separation of dioxolane compounds in aqueous solutions, thereby permitting significantly easier separation and purification.

As mentioned above, the technology described herein provides a method for the conversion of dioxolane compounds into olefins. This conversion method of converting dioxolane compounds into olefins can be readily integrated into a process for generating olefins from diols. Olefin conversion into longer chain hydrocarbons can also be performed by any method for conversion of a given olefin composition into longer chain hydrocarbons.

As an example, dioxolane formation can take place in aqueous media at 313 K using an Amberlyst 15 catalyst (10 wt %) and a 5:1 aldehyde(ketone):BDO ratio. The Amberlyst catalyst is not specifically required for this process, and residual unconverted aldehyde or ketone molecules are recoverable from the aqueous phase. Aldehydes and ketones range from $C_4$-$C_8$ chains resulting in variable dioxolane side chain lengths and either linear or branched side chains. These dioxolanes are readily decanted and may be washed with a saturated bicarbonate solution prior to drying over sodium sulfate. The resulting dioxolanes are analytically pure but can also be run through this process without much further purification.

The conversion of dioxolanes into olefins typically includes reacting dioxolanes with a catalyst, such as a heterogeneous catalyst. In some embodiments, the catalyst is a metal-loaded zeolite. In other embodiments, the zeolite is ZSM-5. In further embodiments, the metal is Cu. In some embodiments, Cu/ZSM-5 was used as the heterogeneous catalyst, although the choice of catalyst is not specific for the disclosed process. For example, dioxolanes can be reacted with Cu/ZSM-5 (e.g., Si/Al ratio of 140) catalyst to form olefins. The reaction temperature can range from 373-773 K. In some embodiments, the reaction conditions for olefin formation without additional oligomerization and cracking products (over the Cu/ZSM-5 catalyst) are: 548 K, 0.33 cm$^3$ s$^{-1}$ H$_2$, 0.01 mol dioxolane (g catalyst)$^{-1}$ h$^{-1}$, 1.6 to 2.1 h$^{-1}$ weight hourly space velocity. Product selectivities at nearly 100% conversion are given in FIG. 2B for a subset of the tested dioxolanes.

The dioxolane conversion into olefins can be accomplished in, for example, pure hydrogen as a carrier gas while also providing a hydrogen source for the reductive reactions that form olefins. Molecular hydrogen is not the only hydrogen source possible for this conversion. Some other possible hydrogen sources include, for example, alcohols (e.g. methanol, ethanol), acids (e.g., acetic acid), or amines.

Dioxolane Synthesis

Dioxolane synthesis was achieved by the reaction of BDO and an aldehyde or ketone catalyzed by a solid acid catalyst (e.g., Amberlyst-15 or Nafion). The synthesis can occur in the presence or absence of water. Table 1 below shows some of the aldehydes or ketones studied and the resulting dioxolanes that were formed.

Table 1. Dioxolane compounds formed from the reaction of BDO and various aldehydes or ketones. Side chain labels correspond to labels in the product distribution figures.

| Aldehyde/Ketone (Side Chain) | Dioxolane Name | Dioxolane Image |
|---|---|---|
| Formaldehyde (N/A) | 4,5-Dimethyl-1,3-dioxolane | |
| Acetaldehyde ($C_2$) | 2,4,5-Trimethyl-1,3-dioxolane | |
| Butyraldehyde ($C_{4, linear}$) | 4,5-Dimethyl-2-propyl-1,3-dioxolane | |
| Isobutyraldehyde ($C_{4, branched}$) | 4,5-Dimethyl-2-(propan-3-yl-1,3-dioxolane | |

-continued

| Aldehyde/Ketone (Side Chain) | Dioxolane Name | Dioxolane Image |
|---|---|---|
| Hexaldehyde ($C_{6,\ linear}$) | 4,5-Dimethyl-2-pentyl-1,3-dioxolane | |
| 2-Ethylbutyraldehyde ($C_{6,\ branched}$) | 4,5-Dimethyl-2-(pentan-3-yl)-1,3-dioxolane | |
| Octanaldehyde ($C_{8,\ linear}$) | 4,5-Dimethyl-2-heptyl-1,3-dioxolane | |
| 2-Ethylhexaldehyde ($C_{8,\ branched}$) | 2-(Heptan-3-yl)-4,5-dimethyl-1,3-dioxolane | |
| Furfural (Furan) | 2-Furan-4,5-dimethyl-1,3-dioxolane | |
| MEK (Methyl-ethyl) | 2-Ethyl-2,4,5-trimethyl-1,3-dioxolane | |
| Acetone (Dimethyl) | 2,2,4,5-Tetramethyl-1,3-dioxolane | |

The dioxolane synthesis forms both an aqueous and an organic phase which readily phase-separate from one another, thus permitting the dioxolane to be isolated by decanting. Formed dioxolanes were characterized by GC-MS and $^1$H and $^{13}$C NMR to identify and confirm the compounds. $^1$H and $^{13}$C NMR spectra helped identify the positioning of carbon and hydrogen atoms within the various dioxolanes. These spectra also indicated the absence of large water quantities in the organic phase as well as the presence of multiple dioxolane stereoisomers, corroborating the multiple peaks observed in the GC-MS injections.

Dioxolane Conversion

The dioxolanes, produced as above, can be converted into a range of hydrocarbon and oxygenate compounds as further described below. Olefins are the target compounds, which can then be further upgraded into fuels or commodity chemicals using additional downstream unit operations. Dioxolanes were thermocatalytically converted to olefins over a Cu/ZSM-5 catalyst in the presence of hydrogen gas.

Figure 2A:
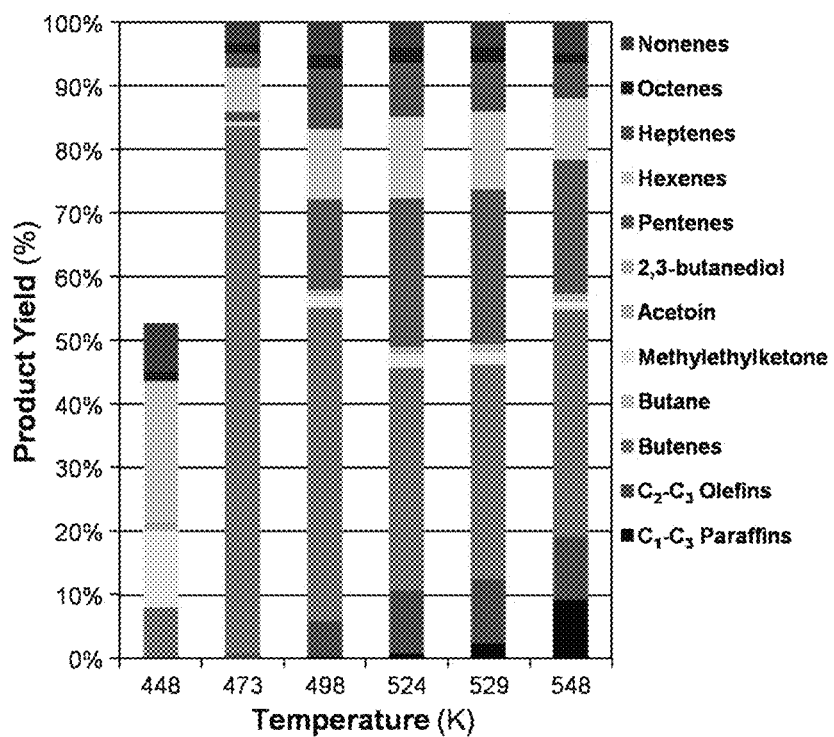
FIGS. 2A-2B. Product distributions (FIG. 2A) and selectivities (FIG. 2B) from the conversion of 4,5-dimethyl-2-propyl-1,3-dioxolane over Cu/ZSM-5 (0.375 cm$^3$ s$^{-1}$ H$_2$, 0.8 h$^{-1}$ WHSV, 0.0055 mol (g catalyst)$^{-1}$ h$^{-1}$) as a function of temperature.
Figure 2B:
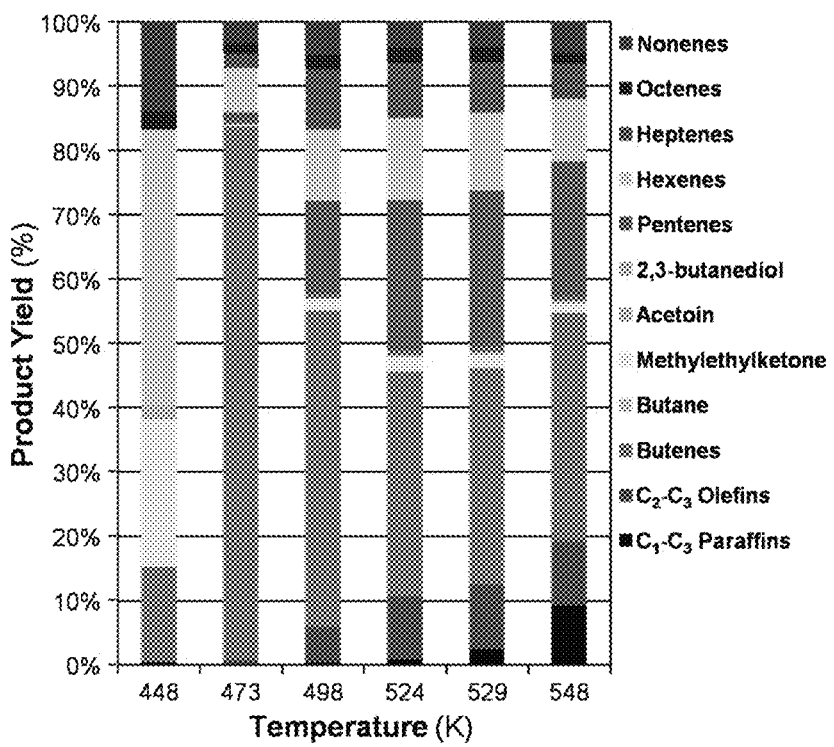
Figure 3A:
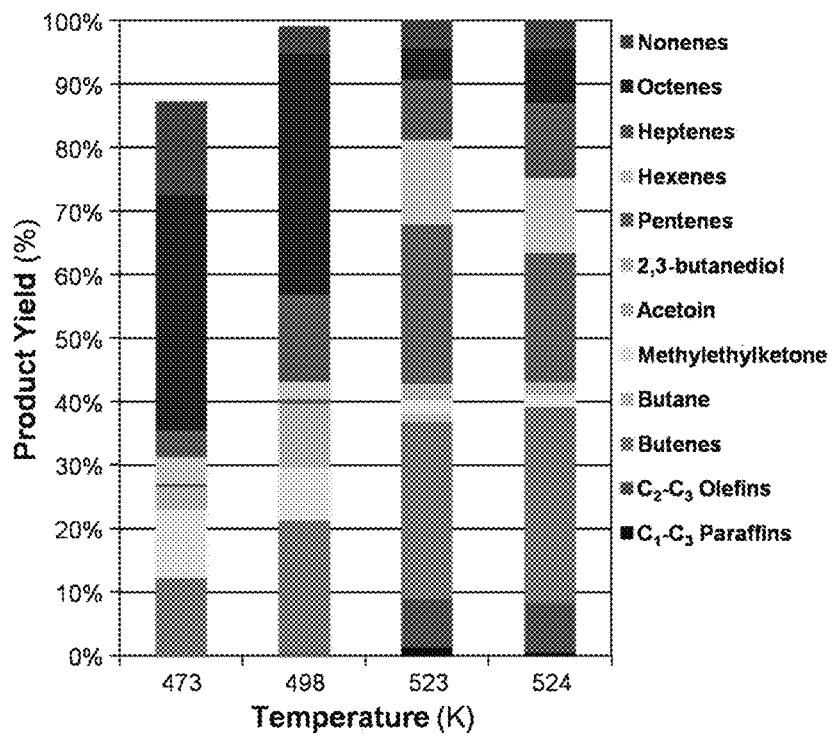
FIGS. 3A-3B. Product distributions (FIG. 3A) and selectivities (FIG. 3B) from the conversion of 2-(heptan-3-yl)-4,5-dimethyl-1,3-dioxolane over Cu/ZSM-5 (0.375 cm$^3$ s$^{-1}$ H$_2$, 0.8 h$^{-1}$ WHSV, 0.0055 mol (g catalyst)$^{-1}$ h$^{-1}$) as a function of temperature.
Figure 3B:
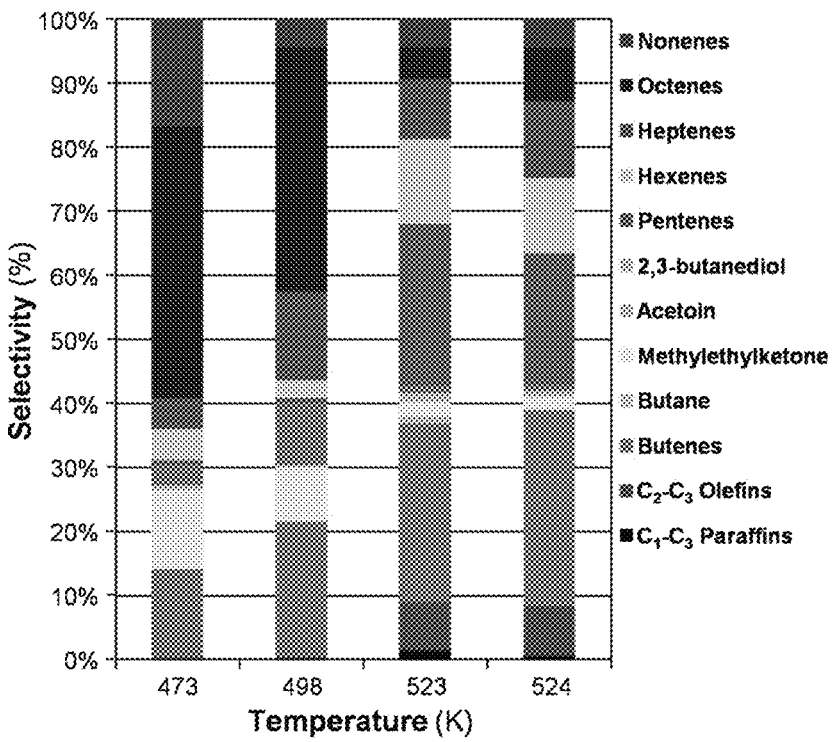

FIGS. 2A-2B show product distributions (FIG. 2A) and selectivities (FIG. 2B) from the conversion of 4,5-dimethyl-2-propyl-1,3-dioxolane over Cu/ZSM-5 (0.375 cm$^3$ s$^{-1}$ H$_2$, 0.8 h$^{-1}$ WHSV, 0.0055 mol (g catalyst)$^{-1}$ h$^{-1}$) as a function of temperature. FIGS. 3A-3B show product distributions (FIG. 3A) and selectivities (FIG. 3B) from the conversion of 2-(heptan-3-yl)-4,5-dimethyl-1,3-dioxolane over Cu/ZSM-5 (0.375 cm$^3$ s$^{-1}$ H$_2$, 0.8 h$^{-1}$ WHSV, 0.0055 mol (g catalyst)$^{-1}$ h⁻¹) as a function of temperature. As shown, conversion increases with temperature for all studied dioxolanes. In general, a significant yield of butenes was observed from all dioxolanes studied, which indicates the conversion of the dioxolane four-carbon chain into MEK and further into butene isomers. Moreover, it has been found that the olefins tend to share a carbon chain length with the aldehyde used for making the dioxolane. For example, octenes are observed from dioxolanes synthesized from $C_8$ aldehydes, and additional butenes are observed from dioxolanes synthesized with $C_4$ aldehydes. As the temperature is increased, hydrocarbon fractions become more diversified, which indicates a range of isomerization, oligomerization, and cracking reactions.

Figure 4A:
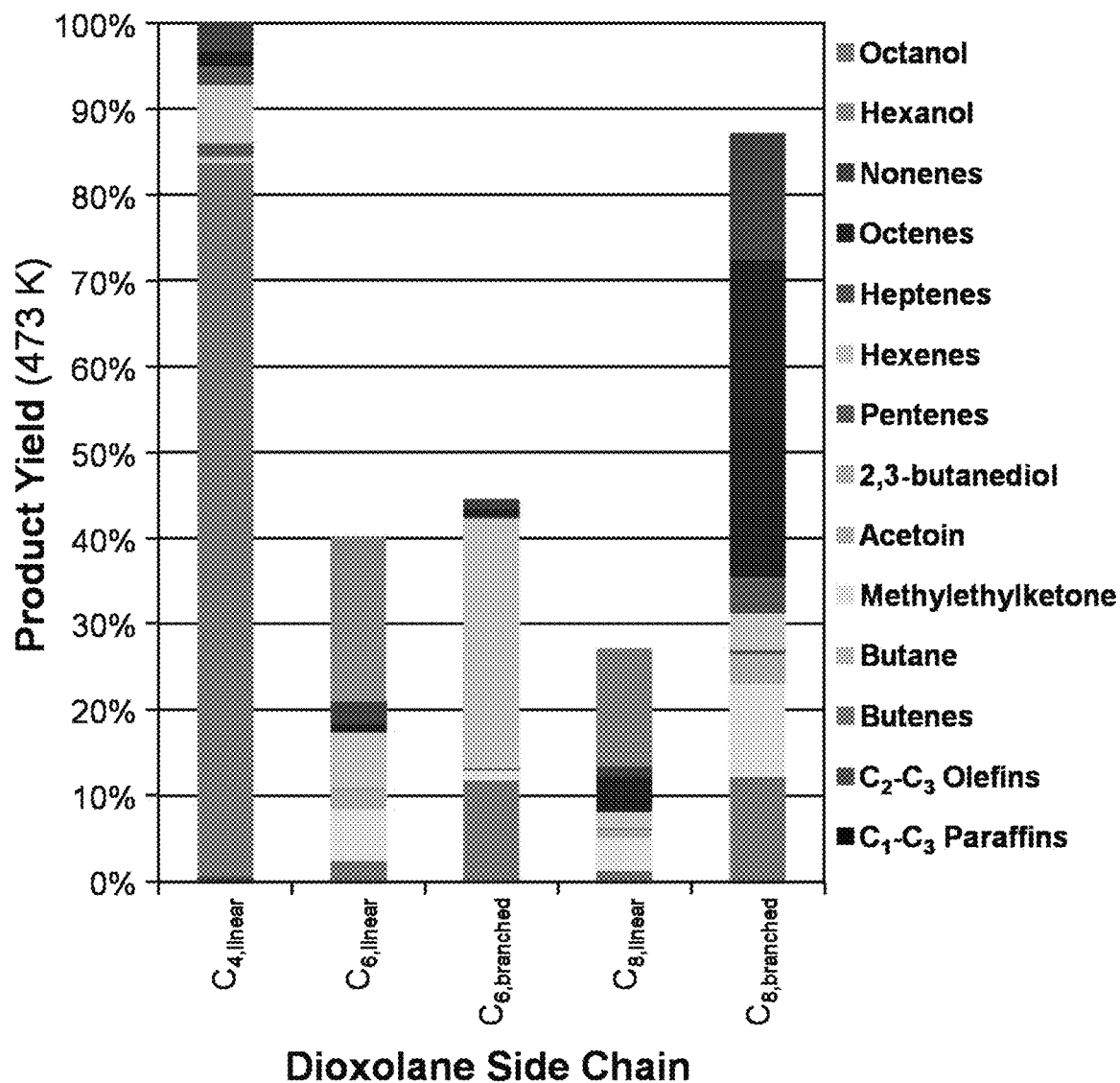
FIGS. 4A-4B. Product distributions (FIG. 4A) and selectivities (FIG. 4B) from dioxolane conversion over Cu/ZSM-5 (473 K, 0.375 cm$^3$ s$^{-1}$ H$_2$, 0.8-1.1 h$^{-1}$ WHSV, ~0.005 mol (g catalyst)$^{-1}$ h$^{-1}$) as a function of dioxolane side chain.
Figure 4B:
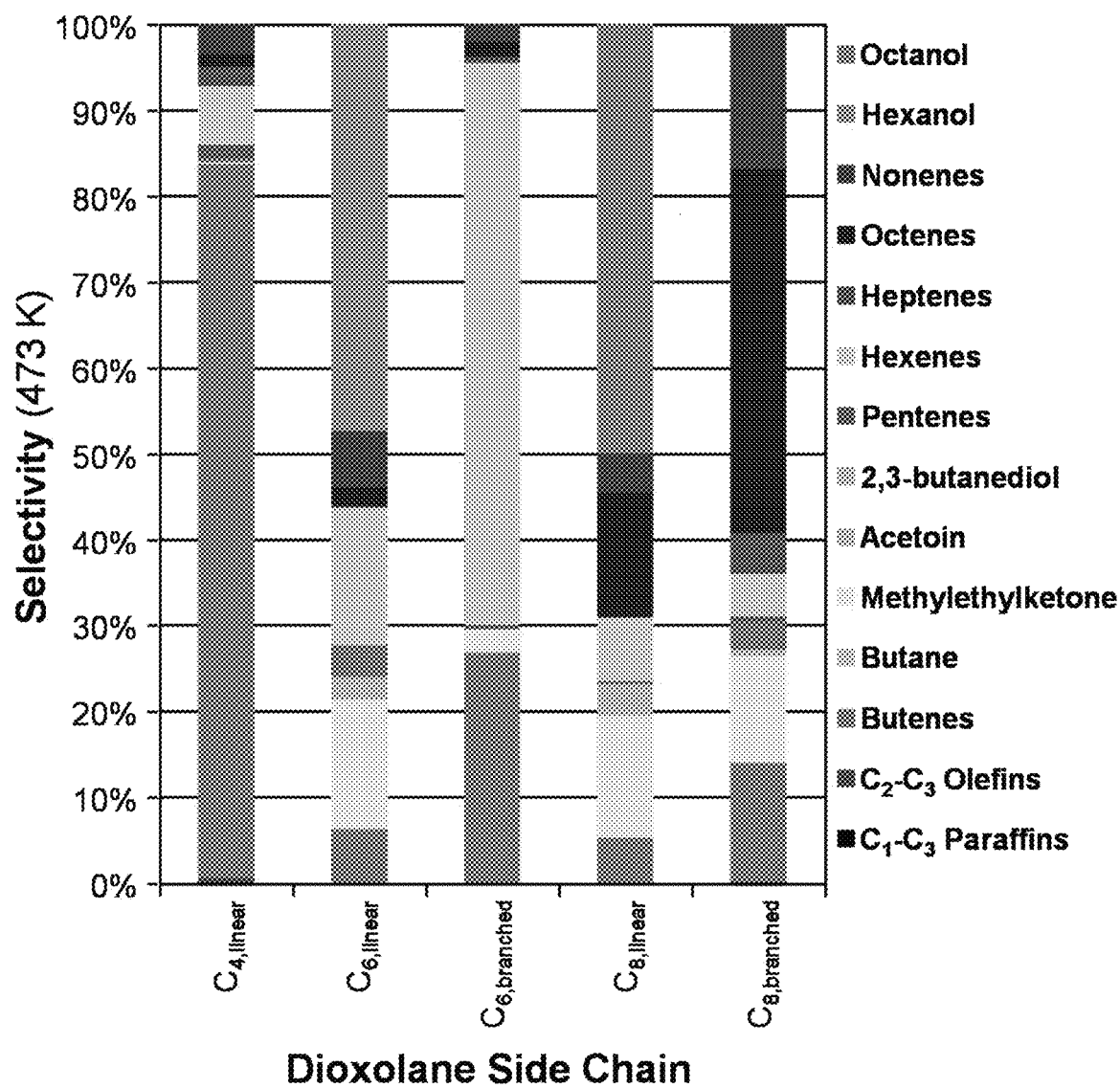
Figure 5A:
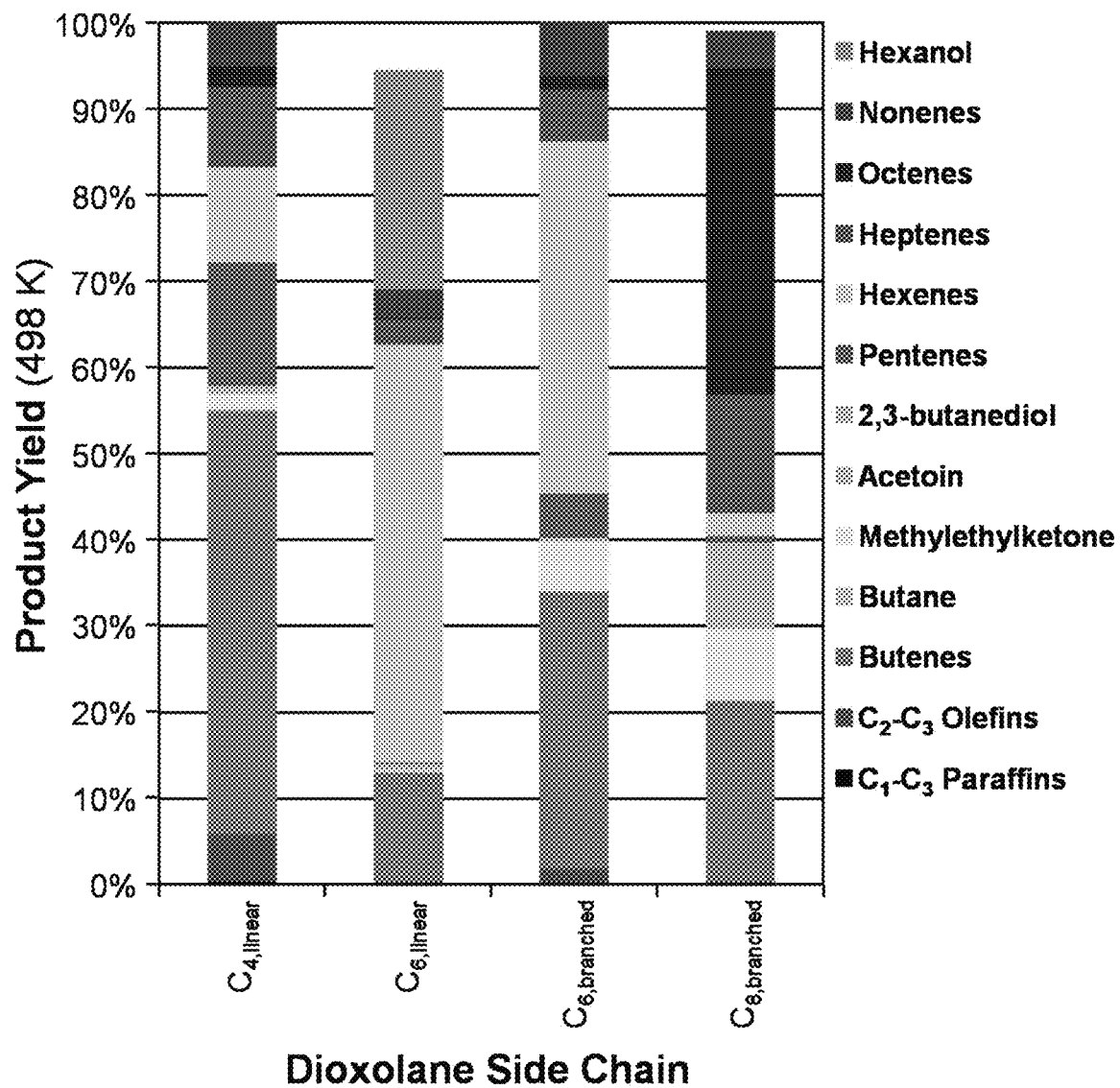
FIGS. 5A-5B. Product distributions (FIG. 5A) and selectivities (FIG. 5B) from dioxolane conversion over Cu/ZSM-5 (498 K, 0.375 cm$^3$ s$^{-1}$ H$_2$, 0.8-1.1 h$^{-1}$ WHSV, ~0.005 mol (g catalyst)$^{-1}$ h$^{-1}$) as a function of dioxolane side chain.
Figure 5B:
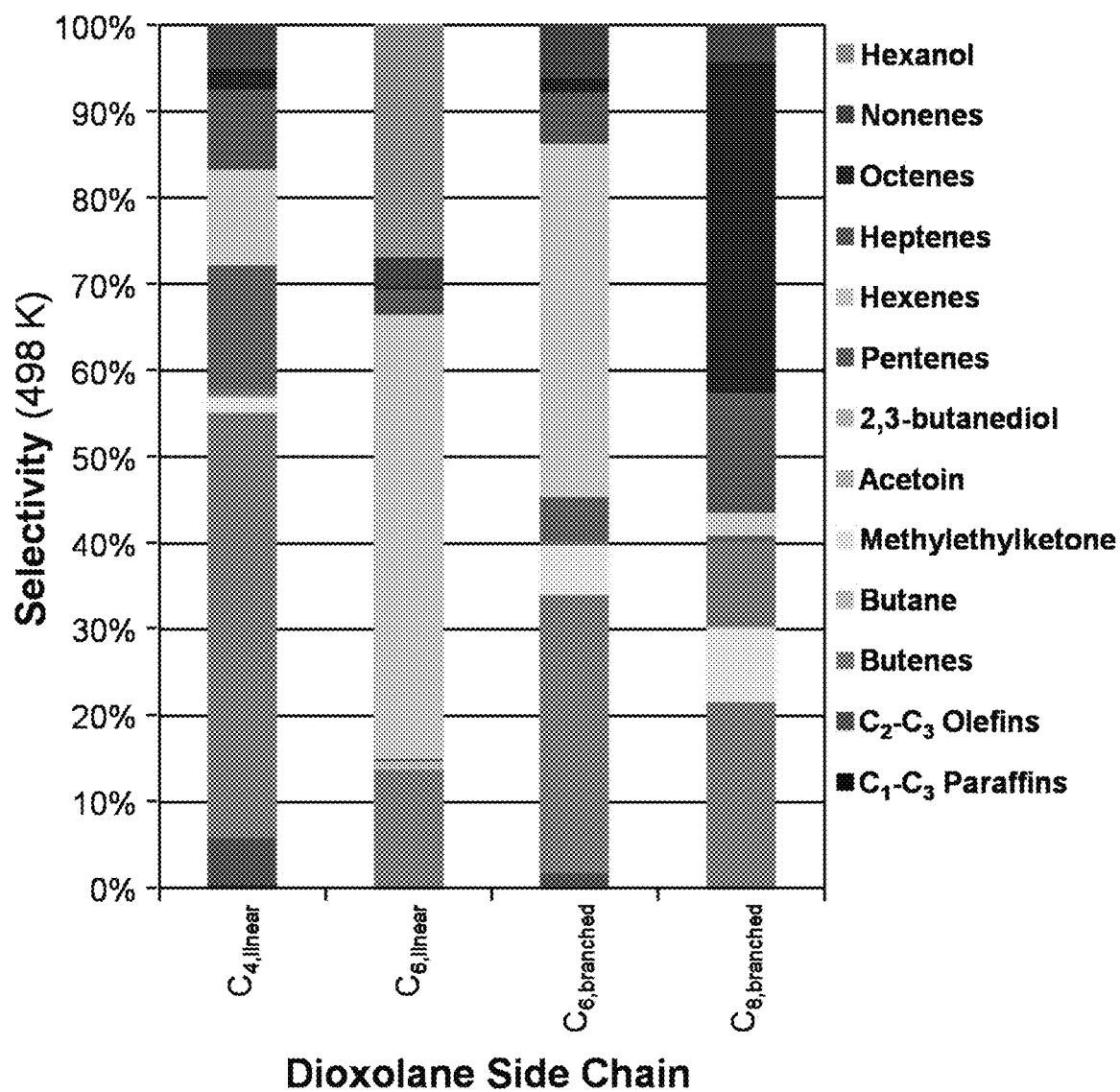
Figure 6A:
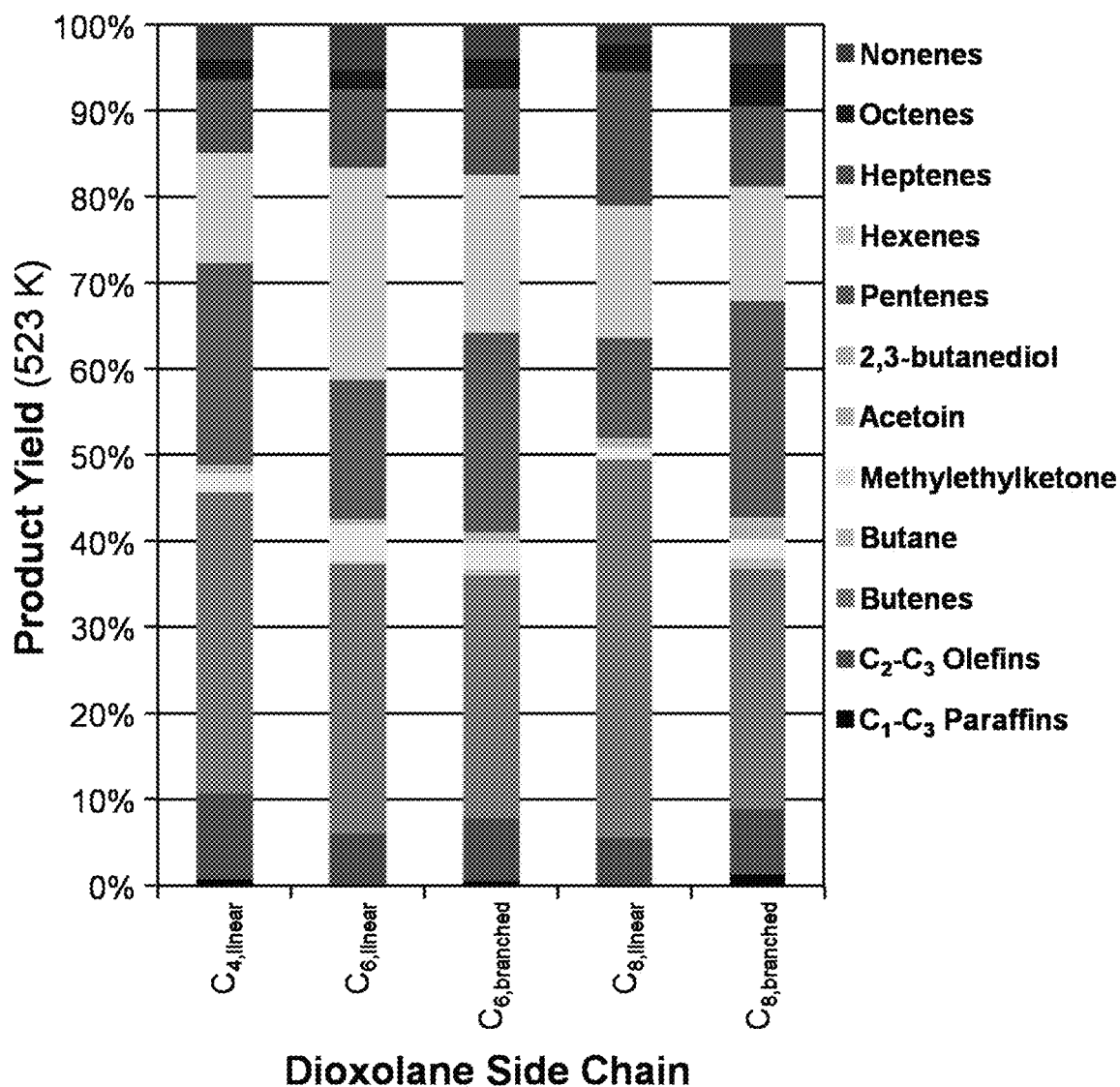
FIGS. 6A-6B. Product distributions (FIG. 6A) and selectivities (FIG. 6B) from dioxolane conversion over Cu/ZSM-5 (523 K, 0.375 cm$^3$ s$^{-1}$ H$_2$, 0.8-1.1 h$^{-1}$ WHSV, ~0.005 mol (g catalyst)$^{-1}$ h$^{-1}$) as a function of dioxolane side chain.
Figure 6B:
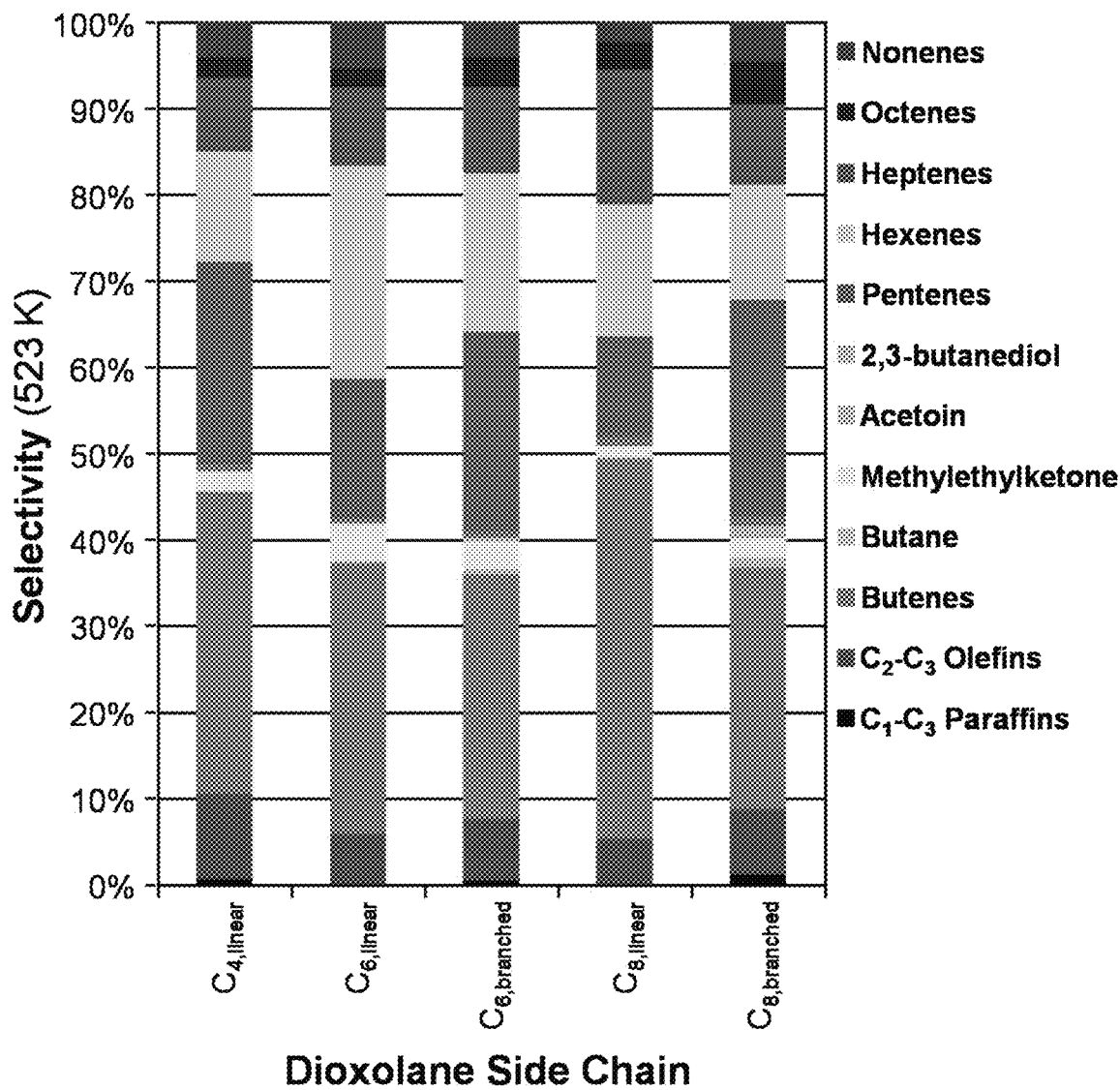

FIGS. 4A-4B show product distributions (FIG. 4A) and selectivities (FIG. 4B) from dioxolane conversion over Cu/ZSM-5 (473 K, 0.375 cm³ s⁻¹ H₂, 0.8-1.1 h⁻¹ WHSV, ~0.005 mol (g catalyst)⁻¹ h⁻¹) as a function of dioxolane side chain. FIGS. 5A-5B show product distributions (FIG. 5A) and selectivities (FIG. 5B) from dioxolane conversion over Cu/ZSM-5 (498 K, 0.375 cm³ s⁻¹ H₂, 0.8-1.1 h⁻¹ WHSV, ~0.005 mol (g catalyst)⁻¹ h⁻¹) as a function of dioxolane side chain. FIGS. 6A-6B show product distributions (FIG. 6A) and selectivities (FIG. 6B) from dioxolane conversion over Cu/ZSM-5 (523 K, 0.375 cm³ s⁻¹ H₂, 0.8-1.1 h⁻¹ WHSV, ~0.005 mol (g catalyst)⁻¹ h⁻¹) as a function of dioxolane side chain.

As shown, conversions and product selectivities vary significantly depending on the side chain composition of the dioxolane reactant. Notably, the "unidentified" category may be the result of the aldehyde generated as the dioxolane is broken down. As the temperature is increased, bulk product distributions become fairly consistent regardless of dioxolane composition. This suggests that the mix of isomerization, oligomerization, and cracking reactions observed at higher temperatures yield an "equilibrated" mixture of olefins and paraffins regardless of the initial dioxolane side chain and associated aldehyde used. Regardless, the bulk olefin selectivities are often 90+% across the range of conversions and temperatures studied here.

While there have been shown and described what are at present considered the preferred embodiments of the invention, those skilled in the art may make various changes and modifications which remain within the scope of the invention defined by the appended claims.

What is claimed is:

1. A method for converting a diol in solution to an olefin fraction, the method comprising:
   (i) reacting a diol of the formula HO—R—OH in solution with a carbonyl-containing molecule of the formula:

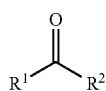

in the presence of an acid catalyst to result in a dioxolane molecule of the formula:

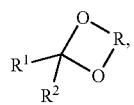

wherein R is a hydrocarbon linker containing 1-12 carbon atoms, and $R^1$ and $R^2$ are independently selected from hydrogen atom and hydrocarbon groups containing 1-12 carbon atoms, wherein $R^1$ and $R^2$ optionally interconnect;
   (ii) removing the dioxolane molecule from the solution by phase separation; and
   (iii) contacting the dioxolane molecule with a metal-loaded zeolite at a temperature of 100-500° C. to convert the dioxolane molecule to an olefin fraction.

2. The method of claim 1, wherein said solution contains water in an amount of at least 20 wt %.

3. The method of claim 1, wherein said solution contains water in an amount of at least 50 wt %.

4. The method of claim 1, wherein the diol comprises 2,3-butanediol.

5. The method of claim 4, wherein the solution is an aqueous 2,3-butanediol fermentation mixture.

6. The method of claim 5, wherein the aqueous 2,3-butanediol fermentation mixture further comprises acetoin and/or ethanol.

7. The method of claim 1, wherein the carbonyl-containing molecule is an aldehyde.

8. The method of claim 1, wherein the carbonyl-containing molecule is a ketone.

9. The method of claim 1, wherein the carbonyl-containing molecule is formaldehyde or acetaldehyde.

10. The method of claim 1, wherein the carbonyl-containing molecule is butyraldehyde or isobutyraldehyde.

11. The method of claim 1, wherein the metal-loaded zeolite is a metal-loaded beta zeolite.

12. The method of claim 1, wherein the metal-loaded zeolite is a metal-loaded pentasil zeolite.

13. The method of claim 12, wherein the metal-loaded zeolite is a metal-loaded ZSM-5 type of zeolite.

14. The method of claim 1, wherein the metal in the metal-loaded zeolite is selected from the group consisting of copper, silver, gold, nickel, palladium, platinum, rhodium, iridium, and ruthenium.

15. The method of claim 1, wherein the metal is present in the metal-loaded zeolite in an amount of 1-30 wt % by weight of the zeolite.

16. The method of claim 1, wherein the metal-loaded zeolite is Cu-loaded ZSM-5.

17. The method of claim 1, wherein the metal-loaded zeolite is Cu-loaded beta zeolite.

18. The method of claim 1, wherein step (iii) is performed in the presence of a carrier gas.

19. The method of claim 18, wherein the carrier comprises an inert gas.

20. The method of claim 18, wherein the carrier gas comprises hydrogen gas.

21. The method of claim 1, wherein after step (ii) but before step (iii) the dioxolane molecule is washed with a saturated bicarbonate solution.

22. The method of claim 1, wherein after step (ii) but before step (iii) the dioxolane molecule is substantially removed of water.

23. The method of claim 1, wherein the process achieves at least 70% selectivity in butenes.

24. The method of claim 1, wherein the process achieves less than 20% ethylene in the olefin fraction.

25. The method of claim 1, wherein the process achieves less than 10% ethylene in the olefin fraction.

26. The method of claim 1, wherein the process achieves less than 5% ethylene in the olefin fraction.

27. The method of claim 1, further comprising: (iv) oligomerizing the olefin fraction to produce longer chain hydrocarbons.

\* \* \* \* \*